(12) United States Patent
Asai

(10) Patent No.: US 6,630,338 B2
(45) Date of Patent: *Oct. 7, 2003

(54) REMOVING DEACETYLASE CONTAMINANT FROM CEPHALOSPORIN C ACYLASE USING CATIONIC SURFACTANT

(75) Inventor: Katsushi Asai, Toyonaka (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/566,721

(22) Filed: May 9, 2000

(65) Prior Publication Data

US 2001/0006804 A1 Jul. 5, 2001

Related U.S. Application Data

(63) Continuation of application No. 09/147,678, filed as application No. PCT/JP97/02663 on Jul. 30, 1997, now Pat. No. 6,165,758.

(30) Foreign Application Priority Data

Aug. 12, 1996 (JP) .............................. 8-212383
Aug. 12, 1996 (JP) .............................. 8-212387

(51) Int. Cl.[7] .......................... C12N 9/14; C12N 11/08; C12N 11/14; C12P 35/06; C12P 35/02
(52) U.S. Cl. .......................... 435/195; 435/49; 435/51; 435/176; 435/177; 435/180; 435/816
(58) Field of Search .............................. 435/49, 50, 174, 435/177, 180, 814, 815

(56) References Cited

U.S. PATENT DOCUMENTS

| 3,728,224 A | | 4/1973 | Borglum |
| 3,794,562 A | | 2/1974 | Bergmeyer et al. |
| 4,055,469 A | * | 10/1977 | Snoke et al. ................. 435/183 |
| 4,250,260 A | * | 2/1981 | Rohrbach et al. ........... 435/176 |
| 4,634,673 A | | 1/1987 | Johnson et al. ............. 435/234 |
| 4,931,498 A | * | 6/1990 | Pidgeon ..................... 525/54.1 |
| 5,190,864 A | * | 3/1993 | Giese et al. ................. 435/176 |

FOREIGN PATENT DOCUMENTS

EP  0 475 652  3/1992

OTHER PUBLICATIONS

"Separation and Purification of Penicillin Acylase from *Escherichia coli* Using AOT Reverse Micilles", Biotechnology Techniques, vol. 9, No. 4, Apr. 1995, p. 265–270.

Kameda et al., "Studies of Acylase Activity and Micro–organisms", Chemical Pharmaceutical Bulletin, vol. 26, No. 9, Jan. 9, 1978, p. 2698–2704.

* cited by examiner

Primary Examiner—David M. Naff
(74) Attorney, Agent, or Firm—Oblon, Spivak, McClelland, Maier & Neustadt, P.C.

(57) ABSTRACT

An enzyme in a mixture containing the enzyme and a contaminant enzyme is purified by selectively aggregating and precipitating the contaminant enzyme with a surfactant. A deacetylase contaminant is separated from Cephalosporin C acylase using a cationic surfactant in an amount of 0.1 to 0.6%. Surfactants include benzylated or methylated cationic surfactants such as alkyl(palm)dimethylbenzyl ammonium chloride, alkyl(palm)trimethyl ammonium chloride and dodecyltrimethyl ammonium chloride. An immobilized enzyme is regenerated using a protease to remove the enzyme from a carrier. The carrier may be a synthetic adsorbent or an ion exchange resin having pores of 100 nm or less in diameter, and the immobilized enzyme is optionally crosslinked. Immobilized cephalosporin C acylase is regenerated using an alkaline or acidic protease.

11 Claims, 1 Drawing Sheet

REMOVING DEACETYLASE CONTAMINANT FROM CEPHALOSPORIN C ACYLASE USING CATIONIC SURFACTANT

This application is a continuation of application Ser. No. 09/147,678, filed Feb. 12, 1999, now U.S. Pat. No. 6,165,758, which was filed as International Application No. PCT/JP97/02663, filed Jul. 30, 1997.

FIELD OF INVENTION

The present invention relates to a method for preparing a bioreactor. More particularly, the present invention relates to a method for purifying an enzyme by the use of a surfactant and a method for regenerating an immobilized enzyme carrier by the use of a protease.

DESCRIPTION OF THE BACKGROUND

A bioreactor is a system technology to reproduce a biochemical reaction in an artificial container, and what is meant by this term has been gradually expanding. As used herein, however, a bioreactor means a reactor wherein an enzyme itself is used as a catalyst. For this end, the enzyme should be immobilized in some way for an economical use of a catalyst. Thus, an immobilized enzyme plays the principal part of a bioreactor. One of the important factors that determine the superiority of an immobilized enzyme is the purity of the enzyme used.

An enzyme protein is purified from a biological sample or cell culture supernatant by appropriately combining the conventionally-known various protein separation techniques according to the properties of the objective enzyme and contaminant protein. At present, predominant separation techniques include, for example, a method utilizing difference in solubilities, such as salting out, solvent precipitation method and the like; a method utilizing difference in molecular weights, such as dialysis, ultrafiltration, gel filtration, polyacrylamide electrophoresis and the like; a method utilizing electric charges, such as ion exchange chromatography and the like; a method utilizing specific affinity, such as affinity chromatography and the like; a method utilizing difference in hydrophobicities, such as reversed phase high performance liquid chromatography and the like; and a method utilizing difference in isoelectric points, such as isoelectric point electrophoresis and the like.

In not a few cases in practice, however, contaminant protein cannot be removed completely from the objective enzyme. This is attributable to the absence of noticeable difference between the objective enzyme and contaminant protein in various physico-chemical properties that the conventional protein separation methods utilize. For example, cephalosporin C acylase derived from Pseudomonas [enzyme that converts cephalosporin C and glutaryl 7-aminocephalosporanic acid (GL7-ACA) to 7-aminocephalosporanic acid (7-ACA); hereinafter to be abbreviated as CC acylase] can be purified up to an approximately 95% purity by repeatedly separating a crude cell extract solution as a starting material by steps such as dialysis, ammonium sulfate fractionation, anion exchange chromatography and the like (Japanese Patent Unexamined Publication No. 5-84078). The contaminant deacetylase, however, cannot be removed by a conventional method because it shows nearly the same behavior on anion exchange resin column as CC acylase. A deacetylase deacetylates 7-ACA to produce deacetyl 7-ACA, causing less yield of 7-ACA. Thus, there remains a strong demand for a novel enzyme purification method capable of separating and removing such undesirable proteins.

Another factor determining the superiority of an immobilized enzyme is the life of an immobilized enzyme carrier. In general terms, enzymes tend to be unstable to heat, strong acid, strong alkali, organic solvent and the like, and easily lose activity even under the conditions preferable for enzyme reactions. An immobilized enzyme shows decreasing enzyme activities with the repeated use thereof, thereby lowering the production efficiency of the objective substance. A degraded immobilized enzyme is generally disposed, but when an ion exchange resin is used as a carrier, a recycled use of the carrier is desirable from environmental and economical considerations.

Conventional methods for regenerating an immobilized enzyme carrier include use of a strong acid or strong alkali to liberate and remove the enzyme from the carrier. However, the enzyme cannot be removed completely from the carrier by this method, which causes drastic decrease in the activity of the immobilized enzyme upon repeated regenerations of carrier and reimmobilizations of enzyme. Particularly when the carrier has fine pores, the enzyme clogs in the fine pores, resulting in appreciable degradation due to regeneration and reimmobilization.

SUMMARY OF THE INVENTION

It is therefore an object of the present invention to provide a method for selectively separating and removing a contaminant enzyme which is undesirable for the objective enzyme and which cannot be removed by conventional separation techniques, thereby to enable production of a highly pure objective enzyme. Another object of the present invention is to provide a method for regenerating an immobilized enzyme carrier, which is capable of efficiently removing an enzyme from a carrier.

The present inventors have conducted intensive studies in an attempt to achieve the above-mentioned objects and had a conception to utilize selective aggregation and precipitation of protein caused by surfactants. Thus, they investigated from various aspects using the system of CC acylase solutions contaminated by deacetylase. The results revealed that the addition of a surfactant, particularly a cationic surfactant, leads to selective aggregation and precipitation of deacetylase, and using this action, the present inventors have succeeded in preparing a standard CC acylase product having a high purity and a high production efficiency of 7-ACA.

The present inventors have also succeeded in removing CC acylase efficiently by allowing a protease to act on an immobilized enzyme obtained by adsorbing CC acylase onto an ion exchange resin carrier and crosslinking CC acylase with glutaraldehyde. Moreover, they have found that, in case of an immobilized enzyme using the above-mentioned enzyme and crosslinking agent, the use of an acidic protease is particularly effective for the removal of enzymes, which resulted in the completion of the present invention.

Accordingly, the present invention provides a method for purifying an enzyme, comprising causing selective aggregation and precipitation of contaminant enzyme by the use of a surfactant. The present invention also provides the above-mentioned method for purifying an enzyme, particularly acylase, wherein the surfactant is cationic. The present invention also provides a method for purifying the above-mentioned acylase, wherein the acylase is cephalosporin C acylase and the contaminant enzyme is deacetylase. The present invention further provides a method for purifying the above-mentioned acylase, wherein the surfactant is a methyl type or benzyl type cationic surfactant, particularly, alkyl (palm)dimethylbenzyl ammonium chloride. In addition, the present invention provides a method for purifying the above-mentioned acylase, wherein the cationic surfactant is used in a concentration of 0.1–0.6%.

The present invention moreover provides a method for regenerating an immobilized enzyme carrier, comprising allowing a protease to act on an immobilized enzyme to remove the enzyme from the carrier, said immobilized enzyme being prepared by binding the enzyme with the carrier, such as a synthetic adsorbent and an ion exchange resin, and optionally crosslinking the enzymes by the use of a crosslinking agent after binding. Particularly, the present invention provides a method for regenerating the above-mentioned carrier, wherein said carrier has fine pores. Moreover, the present invention provides a method for regenerating the above-mentioned carrier, wherein the enzyme is CC acylase. Furthermore, the present invention provides a method for regenerating the above-mentioned carrier, wherein said protease is an acidic protease.

DETAILED DESCRIPTION OF THE INVENTION

Figure 1:
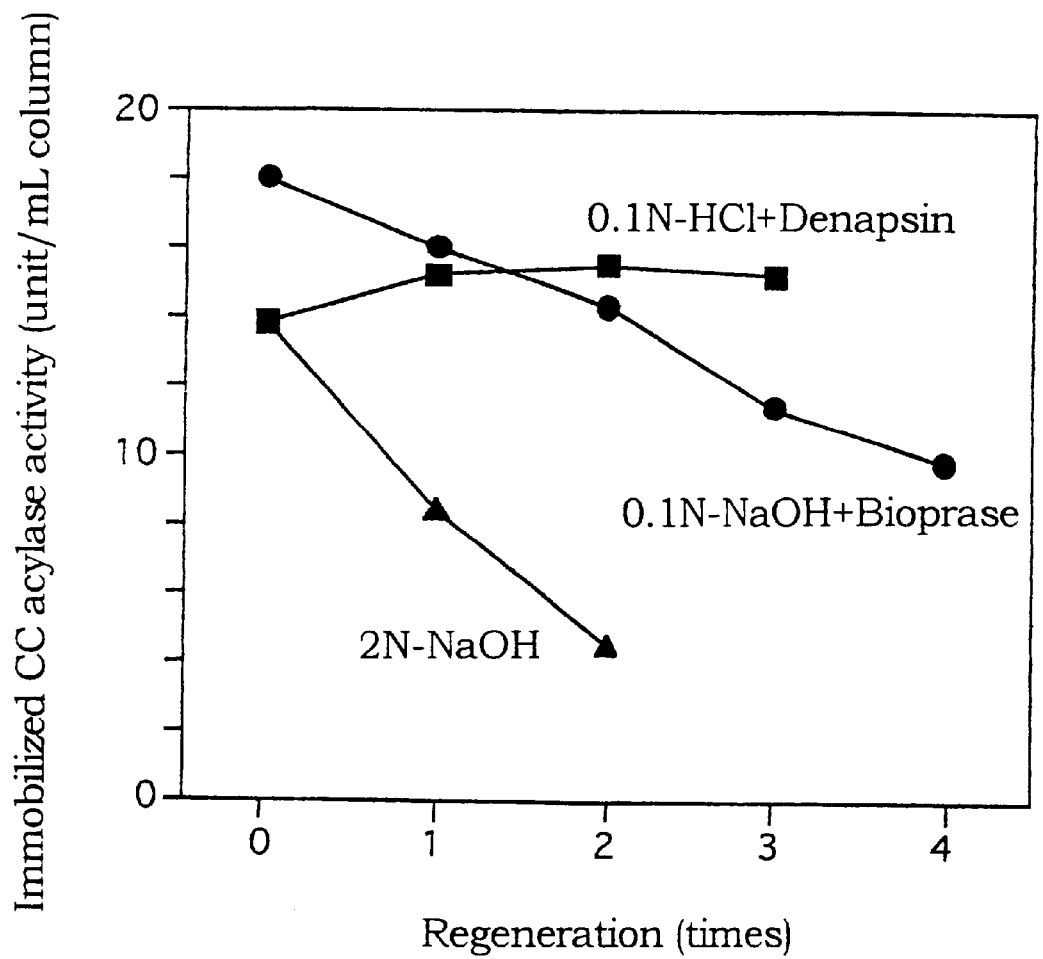
FIG. 1 shows the effect of regeneration conditions on the activity of immobilized CC acylase after regeneration and reimmobilization.

The enzyme applicable to the purification method of the present invention is not subject to any particular limitation as long as it shows less aggregation and less precipitation than other contaminant enzymes with respect to at least one surfactant Preferably, not less than 70% of the enzyme remains in a solution under the conditions wherein not less than 95% of the contaminant enzyme aggregates and precipitates. Examples of preferable enzyme include acylase, particularly CC acylase.

The contaminant enzyme to be removed by the purification method of the present invention should have property to allow easier aggregation and precipitation than the objective enzyme with respect to at least one surfactant. For example, when the objective enzyme is acylase, the contaminant enzyme is exemplified by deacetylase and the lie. The contaminant enzyme may be contained in plurality. When each contaminant enzyme is aggregated and precipitated by different kinds of surfactants, one surfactant is added first to cause aggregation and precipitation of a first contaminant enzyme, followed by removal of the precipitates by centrifugation or filtration, and then, a different surfactant is added to cause aggregation and precipitation of another contaminant enzyme.

The surfactant to be used in the present invention is not particularly limited and can be selected from among cationic, anionic and nonionic surfactants, in accordance with the property of the objective enzyme and contaminant enzyme. When deacetylase, which contaminates an acylase solution, is to be removed, for example, preferably a cationic surfactant, more preferably a methyl type or benzyl type cationic surfactant, particularly methyl and benzyl type cationic surfactants [e.g., alkyl(palm)dimethylbenzyl ammonium chloride and the like], are used.

The surfactant can be used in a concentration that varies depending on the kind of surfactant and the combination of the objective enzyme and contaminant enzyme. The desirable concentration is such that 95% or more of the contaminant enzyme aggregates and precipitates, and 70% or more of the objective enzyme remains in the solution. When the objective enzyme is acylase and the contaminant enzyme is deacetylase, for example, the surfactant is added to the concentration of 0.1–0.6%.

The carrier that can be applied to the inventive method for carrier regeneration is subject to no particular limitation as long as it can be used for immobilization of enzyme by typical carrier binding methods. Examples thereof include natural adsorbents such as active charcoal, acidic clay, kaolinite, celite, alumina, bentonite, silica gel, titanium oxide, chitin, tannin and the like; synthetic adsorbents such as polystyrene resin having a hydrophobic residue (e.g., propyl, butyl, hexyl, phenyl and the like) introduced thereinto, polyacrylamide gel and the like; polysaccharide gel having an ion exchange group; ion exchange resin; and the like. Preferred are synthetic adsorbents and ion exchange resin. The kind of carrier can be appropriately changed according to the property of the enzyme to be immobilized and the like.

The inventive carrier regeneration method is particularly effective when the carrier has fine pores (the fine pores in the present invention mean those having a diameter of 100 nm or less). When an enzyme has been immobilized on a carrier by a carrier binding method and a crosslinking method in combination, for example, a conventional method using a strong acid or a strong alkali fails to dissolve the enzyme insolubilized by forming crosslinks. The enzyme then cloggs in the fine pores to cause string degradation of the carrier. In contrast, the inventive regeneration method using a protease provides efficient removal of the insolubilized enzyme from the carrier, since the insolubilized enzyme is degraded by the action of the protease, resulting in redissolution of the enzyme.

The enzyme to be immobilized on a carrier is subject to no particular limitation as long as it can be bound with the carrier without losing its activity by physical adsorption, ionic bonding and the like, and various enzymes derived from microorganisms, plants and animals can be used. Industrialized enzymes include acylase, amino acylase, invertase, nitrile hydratase, sugar isomerase and the like.

An enzyme can be immobilized onto a carrier by a conventional carrier binding method (an immobilizing method wherein an enzyme is bound with a water insoluble carrier, including a binding method by physical adsorption in the present invention). Particularly, an enzyme is desirably bound with a carrier by ionic bonding, hydrophobic bonding or physical adsorption. When an ion exchange resin is used as a carrier, for example, an equilibrated resin is packed in a column and a suitable buffer containing an enzyme is passed through the column (400–1000 units/mL column), thereby allowing the enzyme to bind with the resin.

When the carrier binding alone is not sufficient to prevent enzyme leakage, enzymes after binding with the carrier are crosslinked with a crosslinking agent and immobilized. Examples of the crosslinking agent include glutaraldehyde, hexamethylene diisoyanate and the like. The crosslinking reaction is performed by washing the immobilized enzyme obtained by the above-mentioned method and circulating a crosslinking agent dissolved in a suitable buffer through a column for approximately 0.5–2 hours. The unreacted functional group in the crosslinking agent needs to be inactivated with an inactivating agent, such as glycine, which is circulated through the column for approximately 0.5–1 hour.

An immobilized enzyme carrier can be regenerated as in the following. An immobilized enzyme prepared by the above-mentioned immobilization method is repeatedly subjected to known enzyme reaction until it loses half the enzyme activity, and a solution (pH 3–5 or pH 9–11) containing 3–50 units/mL of an acidic protease (or alkaline protease) is passed through the column containing said immobilized enzyme, in an about 5–15-fold volume of the column and at a flow rate of 5–20 column volume/hour (hereinafter to be indicated as SV 5–20) for about 1 to 5 hours. Regeneration reaction temperature is 20–60° C., preferably 30–50° C.

The enzyme can be reimmobilized onto a regenerated immobilized carrier in the same manner as in the first immobilization.

EXAMPLES

The present invention is explained in more detail in the following by way of Examples that are for exemplification only, and do not limit the present invention in any way.

Example 1

Separation and removal of deacetylase from CC acylase solution by various surfactants (1) Culture of CC acylase producing bacteria and purification of crude extract solution Mutant CC acylase N-176 producing *E. coli* JM 109 (PCCN 176-2) FERM BP-3047 was cultured according to the method disclosed in Example 3 of Japanese Patent Unexamined Publication No. 584078 and the cells were harvested by centrifugation. The obtained cell pellets were disrupted with a homogenizer and soluble protein component was extracted with water, which was followed by centrifugation to remove debris, whereby a crude extract solution was obtained.

(2) Removal of contaminant deacetylase by surfactant

Polyethyleneimine was added to the crude extract solution obtained in the above-mentioned (1) to allow precipitation of the nucleic acid, which was followed by centrifugation to recover supernatant. This supernatant was applied to DEAE column equilibrated with phosphate buffer (pH 7.0), washed with water and eluted with 0.2M-NaCl. (By this step, β-lactamase, which is the other contaminant enzyme, is selectively recovered and removed in nonadsorbed fraction.) To the obtained eluate was added a cationic surfactant: alkyl(palm)dimethylbenzyl ammonium chloride [trademark: Cation F2-50; manufactured by NOF Corporation hereinafter the same)], alkyl(palm)trimethyl ammonium chloride (trademark: Cation FB) or dodecyltrimethyl ammonium chloride [trademark: Cation BB], an anionic surfactant: alkyl glycine [trademark: Nissan Anon LG] or a nonionic surfactant: polyoxyethylene octylphenyl ether (trademark: Nonion_HS-210) or polyoxyethylenesorbitan monooleate (trademark: Nonion OT-221) to the final concentrations of 0.1, 0.3 and 0.5%, and the mixtures were stood still at room temperature for 16 hours. The activities of CC acylase and deacetylase in each sample before and after the addition of the surfactant were measured and the changes thereof were examined. The enzyme activity was calculated by quantitatively determining 7-ACA and deacetyl 7-ACA produced from GL7-ACA as a substrate. The results are shown in Table 1. Cation F2-50 showed 90% or more of CC acylase residual activity at the concentration of 0.1–0.3% and reduced the activity of contaminant deacetylase to not more than 5%. At the concentration of 0.5%, deacetylase was removed nearly completely. The other two cationic surfactants also showed selective removal of deacetylase at the concentration of 0.5%. When an anionic or nonionic surfactant was used, deacetylase could not be removed completely in the concentration range examined, but the deacetylase activity decreased to nearly half or less almost without decrease of the CC acylase activity.

TABLE 1

Effect on selective removal of contaminant deacetylase by the addition of various surfactants

| Surfactant (trademark) | residual activity[1] (CC acylase/deacetylase) Addition concentration (%) | | | |
|---|---|---|---|---|
| | 0 | 0.1 | 0.3 | 0.5 |
| Cation F2-50 | 100/100 | 95/5 | 92/1 | 70/0 |
| Cation FB | 100/100 | 100/55 | 100/40 | 80/1 |
| Cation BB | 100/100 | 100/55 | 100/45 | 85/5 |
| Nissan Anon LG | 100/100 | 100/60 | 100/50 | 95/30 |
| Nonion HS-210 | 100/100 | 100/50 | 100/50 | 100/45 |
| Nonion TO-221 | 100/100 | 100/50 | 100/50 | 100/45 |

[1]The residual activity is expressed in relative activity based on the enzyme activity before addition of surfactant (addition concentration 0%) as 100.

Example 2

Dissolution of crosslinked CC acylase precipitate by protease

To 10 mM Tris HCl buffer (pH 8.0, 5 mL) containing 67 units/mL of CC acylase N 176 (how to obtain this enzyme is disclosed in Japanese Patent Unexamined Publication No.5-84078) was added 150 mM Tris HCl buffer (pH 8.7, 5 mL) containing 2% glutaraldehyde and the mixture was stirred for 1 hour to allow reaction, whereby a crosslinked product was precipitated. The supernatant was removed by centrifugation and the precipitate was recovered. To the precipitate was added 2N-NaOH, 0.1N-NaOH, 0.1N-NaOH+alkaline protease [Bioprase AL-15 (30 units); manufactured by Nagase Biochemicals Ltd.], 2N-HCl, 0.1N-HCl or 0.1N-HCl+acidic protease [Denapsin (30 units); manufactured by Nagase Biochemicals Ltd.] by 3 mL and the precipitate was immersed therein for 2 hours at 40° C. As a result, addition of NaOH or HCl alone did not cause change in the precipitate, but addition of HCl+acidic protease resulted in the complete dissolution of the precipitate and a clear solution was obtained. While the addition of NaOH+alkaline protease also resulted in nearly complete dissolution of the precipitate, the solution was cloudy and complete dissolution was not achieved. From the above results, it was shown that CC acylase insolubilized by crosslinkng treatment is effectively redissolved by the use of protease, particularly an acidic protease.

Example 3

Regeneration of immobilized CC acylase carrier by protease (1) Preparation of immobilization carrier A brand new styrene-divinyl benzene highly porous strong basic ion exchange resin [80 mL, HPA 25 (having fine pores of diameter 10–100 nm); manufactured by Mitsubishi Chemical Corporation] was immersed in 1N-NaOH methanol=1:1 for one day and packed in a column (350 mm×15 cm). Then, 3-fold volume of 2N-HCl was passed through the column at SV3 and the column was washed with 5-fold volume of water (SV3), whereafter 5-fold volume of 0.1N-HCl was passe through the column at SV3 and the column was washed with water at SV3 until the pH at the outlet of the column became 4 or above.

(2) Immobilization of CC acylase

HPA 25 (80 mL) prepared in the above-mentioned (1) was packed in a column and 10 mM Tris HCl buffer (pH 8.0, 240 mL) containing CC acylase N176 (67 units/mL) was passed through the column at SV3. After washing the column with 240 mL of water (SV3), 60 mM phosphate buffer (pH 8.0, 300 mL) containing 2% glutaraldehyde was circulated at SV20 for one hour while adjusting the pH to 7.5. After crosslinking, the column was washed with 400 mL of water (SV3). Then, 60 mM phosphate buffer (pH 8.0, 300 mL) containing 0.2M glycine was circulated at SV10 for one hour to inactivate unreacted aldehyde groups. Using water (400 mL or more), the column was washed at SV5 to give 82 mL of acylase immobilized on HPA 25.

(3) Production of 7-ACA by immobilized CC acylase

CC Acylase immobilized on HPA 25 (20 mL) and prepared in the above-mentioned (2) was packed in a column with a jacket, and 6.0 mg/mL glutaryl 7-aminocephalosporanic acid (GL7-ACA) solution (100 mL) was circulated for one hour at 20° C. at circulation flow rate of about 70 mL/min while adjusting the pH to 7.75 with NaOH, whereby 7-ACA was obtained. After the reaction, the reaction mixture in the column was pushed out with water and 7-ACA was recovered. The above-mentioned reaction was repeated 100 times (continuous batch reaction), which was taken as one cycle.

(4) Regeneration of immobilization carrier

Using 2N-NaOH, 0.1N-NaOH+Bioprase (3000 ppm, 10 units/mL) or 0.1N-HCl+Denapsin (3000 ppm, 10 units/mL) as a regeneration agent, HPA25 was regenerated every one cycle. The regeneration agent (10-fold volume of carrier) was circulated at 40° C., SV about 20 for 5 hours.

After the regeneration reaction, the above-mentioned steps (1)–(4) were repeated 2 to 4 times, and the CC acylase activity after reimmobilization (2) was determined. The changes of the activities were compared.

The results are shown in FIG. 1. When 2N-NaOH was used as a regeneration agent, the activity of the immobilize CC acylase decreased in nearly half at every cycle, whereas the use of 0.1N-HCl and Denapsin (acidic protease) did not result in decrease of the enzyme activity even after 3 cycles. When 0.1N-NaOH and Bioprase (alkaline protease) were used, the activity of CC acylase decreased at every cycle but in a smaller magnitude as compared to the single use of NaOH, and not less than 50% of the original activity was expressed even after 4 cycles.

The enzyme purification method of the present invention is characterized in that undesirable contaminant enzyme for the objective enzyme, which cannot be removed by a conventional purification method, is separated and removed by utilizing the selective aggregation and precipitation of protein by a surfactant According to the present invention, therefore, a standard enzyme product having a higher purity than the conventional products can be produced. In addition, the method for regenerating an immobilized enzyme carrier of the present invention based on the action of protease on enzyme can remove enzyme from a carrier extremely efficiently, so that a long term continuous recycled use of the carrier is realized. Consequently, the present invention greatly contributes to the reduction of the production cost of a bioreactor and prevention of environmental destruction associated with the waste disposal of carrier.

This application is based on application Nos. 212383/1996 and 212387/1996 filed in Japan, the contents of which are incorporated hereinto by reference. All publications are herein incorporated by reference to the same extent as if each individual publication was specifically described herein.

What is claimed is:

1. A purified cephalosporin C acylase obtained by removing a deacetylase contaminant from a mixture comprising cephalosporin C acylase by adding to the mixture 0.1 to 0.6% of a cationic surfactant for a time and under conditions suitable for reducing the amount or activity of the deacetylase.

2. A method for removing deacetylase activity from a mixture comprising cephalosporin C acylase and a deacetylase contaminant comprising:

adding to the mixture 0.1 to 0.6% of a cationic surfactant for a time and under conditions suitable for reducing the amount or the activity of the deacetylase.

3. The method of claim 2, wherein the deacetylase is removed by centrifugation or filtration.

4. The method of claim 3, wherein said cephalosporin C acylase is purified from a mixture obtained by disrupting bacterial cells, extracting the disrupted cells with water, recovering the supernatant, precipitating nucleic acids by adding polyethyleneimine and recovering the resulting supernatant.

5. The method of claim 2, wherein the cationic surfactant is alkyl(palm)dimethylbenzyl ammonium chloride.

6. The method of claim 2, wherein the cationic surfactant is alkyl(palm)trimethyl ammonium chloride.

7. The method of claim 2, wherein the cationic surfactant is dodecyltrimethyl ammonium chloride.

8. The method of claim 2, wherein said mixture is obtained from cephalosporin C acylase producing bacteria.

9. The method of claim 2, wherein said mixture is obtained from E. coli bacteria that produce cephalosporin C acylase.

10. The method of claim 2, wherein said mixture is obtained from Pseudomonas bacteria that produce cephalosporin C acylase.

11. A cephalosporin C acylase obtained by the method of claim 2.

* * * * *